United States Patent [19] [11] 4,235,808
Drake [45] Nov. 25, 1980

[54] PURIFICATION OF UNSATURATED DINITRILES BY CONTACTING WITH CHI-ALUMINA PRIOR TO HYDROGENATION

[75] Inventor: Charles A. Drake, Nowata, Okla.

[73] Assignee: Phillips Petroleum Company, Bartlesville, Okla.

[21] Appl. No.: 939,168

[22] Filed: Sep. 1, 1978

[51] Int. Cl.$^3$ .................. C07C 120/00; C07C 121/28; C07C 121/46; C07C 121/66
[52] U.S. Cl. ............................ 260/465.8 R; 260/464; 260/465 H; 564/491; 564/511
[58] Field of Search ........ 260/583 K, 583 P, 465.8 R, 260/465 H, 464

[56] References Cited

U.S. PATENT DOCUMENTS

| | | | |
|---|---|---|---|
| 3,283,803 | 11/1966 | Phillips, Jr. et al. | 159/47 |
| 3,293,298 | 12/1966 | Szabo | 260/583 K |
| 3,408,397 | 10/1968 | Feldman et al. | 260/583 K |

OTHER PUBLICATIONS

Wiberg, Lab. Technique in Org. Chem., 1960, pp.155–156 McGraw-Hill, N.Y., N.Y.
Kirk–Othmer, "Encyclopedia of Chem. Technology," vol. 2, 2nd ed., 1963, pp. 48–49.

*Primary Examiner*—Joseph Paul Brust

[57] ABSTRACT

The lifetime and activity of catalysts for the hydrogenation of unsaturated dinitriles are increased by contacting the unsaturated dinitriles with chi-alumina prior to hydrogenation. This process additionally reduces the level of olefin unsaturation in the hydrogenation product below the level of olefin unsaturation of similarly hydrogenated unsaturated dinitriles which have not been contacted with chi-alumina prior to hydrogenation.

19 Claims, No Drawings

PURIFICATION OF UNSATURATED DINITRILES BY CONTACTING WITH CHI-ALUMINA PRIOR TO HYDROGENATION

The invention relates generally to the catalytic hydrogenation of unsaturated dinitriles to saturated dinitriles and/or saturated diamines. In general, various processes for the catalytic hydrogenation of unsaturated dinitriles to saturated diamines are known to the art. Group VIII metal catalysts such as cobalt, nickel, ruthenium, rhodium, or palladium have been employed as effective catalysts for the hydrogenation of various feedstocks in these processes. It has been found that, during such catalytic hydrogenation processes, the catalyst becomes poisoned which results in a short catalyst life as evidenced by the early appearance of olefinic unsaturation in the hydrogenation product. For commercial use, a long catalyst life is desired so that less frequent changes of catalyst are required and a product with lower average levels of unsaturation can be produced. It would therefore be highly desirable to provide a method of purifying the unsaturated aliphatic dinitrile to prevent the rapid poisoning of the catalyst.

I have discovered that the catalytic hydrogenation of olefinically unsaturated dinitriles can be more efficiently performed and the catalysts used therein more efficiently utilized if the olefinically unsaturated dinitriles are contacted with chi-alumina so as to produce a treated feedstock prior to subjecting said treated feedstock to suitable hydrogenation conditions in the presence of hydrogen and a suitable hydrogenation catalyst so as to effect hydrogenation of the olefinically unsaturated dinitrile compounds.

The present invention is concerned with the more efficient utilization of hydrogenation catalysts in the hydrogenation of olefinically unsaturated dinitriles to saturated dinitriles or saturated diamines. In one embodiment the invention is concerned with the more efficient utilization of palladium hydrogenation catalysts in the hydrogenation of olefinically unsaturated dinitriles. In another embodiment the invention is concerned with the more efficient utilization of ruthenium hydrogenation catalysts in the hydrogenation of olefinically unsaturated dinitriles. Suitable olefinically unsaturated dinitriles comprise the reaction product obtained by contacting at least one olefinic hydrocarbon reactant, such as isobutylene, at least one olefinically unsaturated mononitrile reactant, such as acrylonitrile, and at least one monoadduct reaction product of an olefinic hydrocarbon compound, such as isobutylene, and an olefinically unsaturated mononitrile compound, such as acrylonitrile. Each of the one or more olefinically unsaturated mononitrile reactants and each of the one or more olefinically unsaturated mononitrile compounds contains a cyano group attached to a carbon atom adjacent and doubly bonded to a carbon atom which is attached to at least one hydrogen atom. Each of the one or more olefinic hydrocarbon reactants and each of the one or more hydrocarbon compounds has an at least one olefinic linkage and has joined to one of the doubly bonded carbon atoms another carbon atom having at least one hydrogen atom attached thereto. The unsaturated dinitriles can be termed the hydrogenation substrate in the present invention. Suitable hydrogenation substrates of the present invention can contain from 7 to 30 carbon atoms per molecule and preferably from 9 to 12 carbon atoms per molecule. Examples of suitable hydrogenation substrates include 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, 2,6-dimethyl-4-methyleneheptanedinitrile and the like.

In accordance with the present invention, the hydrogenation substrate is purified or treated by contacting the substrate with chi-alumina before hydrogenation. Suitable alumina for use in purification of the hydrogenation substrate has a chi-crystal structure as identified by its X-ray pattern. The alumina can have particles of any suitable size, but generally the particles are of a size in the range of about 0.005 to about 2 mm, preferably in the range of about 0.01 to about 1 mm. The hydrogenation substrate can be brought into contact with the chi-alumina in a suitable non-deleterious atmosphere. Such a non-deleterious atmosphere can be provided by an inert atmosphere such as nitrogen, argon, helium, or the like. The hydrogenation substrate can be brought into contact with the chi-alumina in any suitable form, but generally in the form of an undiluted liquid or in one or more diluents such as hydrocarbons, alcohols, cyclic ethers and acyclic ethers or the like. For example, the substrate can suitably be passed through a column containing the chi-alumina.

Temperatures used during the purification of the substrate can be any suitable purification temperature, but generally will be in the range of about $-10°$ to about $150°$ C., and preferably in the range of about $0°$ to about $75°$ C. The pressure of the inert gas can be any suitable purification pressure, but will generally be in the range of about 0.01 to about 100 atmospheres (0.001 to 10.1 MPa), and preferably in the range from about 0.1 to about 5 atmospheres (0.01 to 0.51 MPa). Flow rates of the substrate through the chi-alumina can be any suitable flow rate, but will generally be in the range of about 0.01 to about 50, and preferably in a range of about 0.1 to about 5 ml of substrate or olefinically unsaturated dinitriles per ml of chi-alumina per hour. The contact time between the substrate and the chi-alumina can be of any suitable amount which will provide purification of the substrate.

Suitable hydrogenation catalysts for utilization in the present invention include those based on palladium or ruthenium. For example, the catalysts can be elemental ruthenium, elemental palladium, or compounds of ruthenium or palladium which are reducible by hydrogen under suitable hydrogenation conditions to finely divided elemental ruthenium or palladium. Examples of such suitable hydrogen-reducible compounds include oxides, halides, nitrates, oxalates, acetates, carbamates, propionates, tartrates, hydroxides, and the like and mixtures of two or more thereof. Specific examples include elemental ruthenium, ruthenium oxide, ruthenium chloride, ruthenium nitrate, ruthenium acetate, ruthenium carbonate, ruthenium hydroxide, elemental palladium, palladium oxide, palladium chloride, palladium nitrate, palladium oxalate, palladium acetate and palladium hydroxide, and the like.

In the practice of the present invention the palladium catalysts are generally used for the hydrogenation of the olefinic unsaturation of unsaturated dinitriles to give saturated dinitriles. The ruthenium catalysts are generally used for the reduction of the unsaturated and/or saturated dinitriles to saturated diamines.

It is preferable in the practice of the present invention to employ catalytic amounts of elemental ruthenium or elemental palladium on a solid catalyst carrier which does not deleteriously affect the catalytic hydrogenation process of the invention. Such supports include, for example, carbon, kieselguhr, silica, alumina, silica-alumina, calcium carbonate, asbestos, pumice, clays, and the like, and mixtures of two or more thereof. The ruthenium or palladium can be added to the catalytic support by any of the methods well known in the art. For example, the supported catalyst can be prepared by dry mixing the components or by impregnating this support with a solution or dispersion of ruthenium or palladium in elemental form or in the form of reducible compounds thereof. The supported catalysts can be pretreated with hydrogen to reduce the palladium or ruthenium compounds, or such reduction can be achieved in the hydrogenation reactor. When a support is employed, the amount of elemental ruthenium or palladium on the support material will generally be in the range of about 0.05 to about 20 weight percent, and preferably in the range of about 0.1 to about 10 weight percent based on the weight of the total catalyst components. Examples of suitable catalysts include ruthenium or palladium on alumina, each having a catalytic metal content of about 5 weight percent based on the total weight of the catalyst and support material. Other suitable catalysts include palladium on charcoal (10 weight percent palladium), ruthenium dioxide, and ruthenium on charcoal (5 weight percent ruthenium). The specifically named catalysts are commercially available catalytic materials.

The amount of catalyst employed in a batch hydrogenation process of the present invention can be expressed in terms of the weight percent of catalytic metal based on the weight of compound being hydrogenated. The amount of catalytic metal can be any suitable quantity, but generally will be in the range of about 0.01 to about 20, and preferably in the range of about 0.05 to about 5, weight percent of palladium or ruthenium based on the hydrogenation substrate. The amount of catalyst used for a continuous hydrogenation process in accordance with the present invention can be any suitable quantity, but generally is such that a liquid hourly space velocity (LHSV) in the range of about 0.01 to about 10, and preferably in the range from about 0.05 to about 5, volumes of unsaturated dinitrile plus diluent per volume of catalyst will be attained.

The hydrogen pressure utilized in the hydrogenation process in accordance with the present invention can be any suitable pressure but is generally within the range of about 500 to about 5000 psig (3.5 to 35 MPa) and preferably in the range of about 1000 to 3000 psig (6.9 to 20.7 MPa). The temperature utilized under the hydrogenation conditions of the present invention using palladium catalysts can be of any suitable value, but is generally in the range of about 20° to about 250° C. and preferably in the range of about 80° to about 170° C. The temperature utilized under the hydrogenation conditions of the present invention when using ruthenium catalysts can be of any value, but is generally in the range of from 80° to about 250° C. and preferably in the range from about 125° to about 170° C. Any suitable time period can be employed in the hydrogenation process in accordance with the present invention, but will generally be in the range of about 15 minutes to about 5 hours for a batch process.

Any suitable diluent can be employed in the hydrogenation process of the present invention when palladium is used as a catalyst, but generally the diluent will be selected from the group consisting of alcohols having 1 to 12 carbon atoms per molecule, unsubstituted acyclic or unsubstituted cyclic ethers having from 4 to 12 carbon atoms per molecule, and mixtures of two or more thereof. The presently preferred diluent when palladium is used as a catalyst is methanol.

Any suitable diluent can be employed in the hydrogenation process of the present invention when ruthenium is used as a catalyst, but generally the diluent will be selected from the group consisting of alcohols having 2 to 12 carbon atoms per molecule, unsubstituted acyclic or unsubstituted cyclic ethers having 4 to 12 carbon atoms per molecule, and mixtures of two or more thereof. Currently preferred diluents for use with ruthenium catalysts are tertiary alcohols, the more preferred diluent being tertiary-butyl alcohol.

Any suitable suppressant can be employed to suppress undesirable side reactions in the hydrogenation of unsaturated dinitriles, but generally ammonia is employed in the hydrogenation of unsaturated dinitriles with ruthenium catalysts as a means of suppressing undesirable side reactions such as the formation of secondary and tertiary amines. In general, the mol ratio of ammonia to cyano groups, there being two cyano groups per unsaturated dinitrile molecule, will be in the range of about 1:1 to about 25:1 and preferably in the range of about 7:1 to about 15:1.

Recovery of the desired end product, the saturated diamines or dinitriles, as well as any resulting reaction byproducts, any unconsumed reactants, ammonia, hydrogen, and/or diluents, can be carried out by any conventional separation means. In general, at the conclusion of the catalytic hydrogenation process, the reaction zone effluent is cooled and depressurized with the recovery, if desired, of any ammonia or diluent which is vented from the reaction zone effluent during the depressurization operation. The ammonia or diluent can be returned or recycled to the hydrogenation zone if desired. The reaction products can be separated from the catalyst by conventional filtration means. The filtrate containing the hydrogenation product can be conveniently separated from any reaction byproducts or any diluent remaining in the filtrate by any conventional fractional distillation.

In each of the illustrative examples which follow, the olefinic substrate which undergoes hydrogenation is an unsaturated dinitrile mixture obtained by the reaction of isobutylene, acrylonitrile and the monoadduct of isobutylene and acrylonitrile. This unsaturated dinitrile mixture comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. For convenience, the above mixture will be described as diadduct in the examples presented below. The above-described diadduct can be hydrogenated to produce a saturated diamine for use in the preparation of polyamides and other polymers. In such applications it has been found highly desirable that essentially none of the olefinic unsaturation remains in the final hydrogenation product. It is thus important that the carbon-carbon double bonds in the diadduct be reduced efficiently in the hydrogenation process employed.

EXAMPLE I

Two runs were conducted employing the hydrogenation of the olefinic unsaturation of diadduct over a palladium catalyst composition. Each of the two runs was carried out in a 0.5 inch (12.7 mm) diameter×20 inch (508 mm) length laboratory continuous reactor to which 40 grams (about 45 ml) of a catalyst composition of palladium on gamma-alumina (0.5 weight percent palladium) was charged. The palladium on gamma-alumina was pre-reduced at 150° C. and 1500 psig (10.3 MPa) for 4 hours with a hydrogen flow of 1 liter per minute. Diadduct was fed as a 10 weight percent solution in methanol to the reactor at a liquid hourly space velocity of about 2 volumes of unsaturated dinitrile plus diluent (methanol) per volume of catalyst. Reactor conditions during hydrogenation were 1500 psig pressure (10.3 MPa), 100° C., and 1 liter per minute hydrogen flow. In Run No. 1 the diadduct and diluent feedstock was introduced directly into the reactor. In Run No. 2 the diadduct and diluent feedstock was passed by gravity feed through a 20 inch (508 mm) long by 1 inch (25.4 mm) diameter column of chi-alumina at 25° C., under atmospheric pressure, and at a rate of about 2 ml per ml of chi-alumina per hour. The particle size of the chi-alumina was in the range from about 0.05 to about 0.2 mm. The hydrogenation product of each run was analyzed by gas-liquid chromatography after the methanol solvent had been removed under reduced pressure. The results of the two runs are presented below in Table I as amounts of olefinic unsaturation in the saturated dinitrile product.

TABLE I

| Run No. | Purification Treatment | Extent of Unsaturation in Product (a) After Indicated No. of Hours | |
|---|---|---|---|
| | | 3 hours | 18 hours |
| 1 | None | 3.7% | 9.5% |
| 2 | Chi-Alumina | 1.5% | 5.1% |

(a) Expressed as a weight percent olefinic unsaturation based on product at the stated time during the run.

The runs show that the product from the hydrogenation of chi-alumina purified diadduct contains less olefinic unsaturation than the product from the hydrogenation of untreated diadduct.

EXAMPLE II

Five runs were carried out in which the diadduct was hydrogenated to the saturated diamine in a one step process employing as a catalyst composition ruthenium on gamma-alumina (0.5 weight percent ruthenium). Each run was carried out in a 0.5 inch (12.7 mm) diameter×20 inch (508 mm) length laboratory continuous reactor which was charged with 15 grams (about 18 ml) of the above-noted ruthenium on gamma-alumina catalyst composition. The reactor was flushed with nitrogen and the catalyst was activated at 150° C., 1500 psig (10.3 MPa), and a 1 liter per minute hydrogen flow. In each of the runs, a solution composed of 9 weight percent diadduct, 9 weight percent ammonia, and 82 weight percent tertiary-butyl alcohol was fed at a liquid hourly space velocity of about 3.3 volumes of unsaturated dinitrile plus ammonia plus tertiary-butyl alcohol per volume of catalyst to the reactor. The reactor conditions during hydrogenation were 1500 psig pressure (10.3 MPa), 100° C., and 1 liter per minute hydrogen flow. Samples were collected at regular time intervals and analyzed by gas-liquid chromatography after evaporating the ammonia and the tertiary-butyl alcohol diluent. In Run No. 3, the feedstock of diadduct, diluent and ammonia was introduced directly into the reactor. In Runs Nos. 4 and 5 the diadduct was passed through a column of chi-alumina before introduction into the reactor. In Runs Nos. 6 and 7 the diadduct was passed through a column of gamma-alumina before introduction into the reactor. The results of these five runs are presented in Table II below in terms of the weight percent olefinic unsaturated compounds present in the saturated diamine product.

TABLE II

| Run No. | Purification Treatment | Extent of Unsaturation in Product[a] After Indicated No. of Hours | | | | |
|---|---|---|---|---|---|---|
| | | 1 hr | 3 hr | 5 hr | 7 hr | 11 hr |
| 3 | None | 2.86% | 4.05% | (f) | (f) | (f) |
| 4 | Chi-alumina[b] | 0.80% | 1.04% | 0.93% | 1.91% | (f) |
| 5 | Chi-Alumina[c] | 0.21% | 0.24% | 0.41% | 0.67% | 1.48% |
| 6 | Gamma-Alumina[d] | 1.26% | 2.39% | 2.97% | 11.89% | (f) |
| 7 | Gamma-Alumina[e] | (g) | (g) | 2.54% | 5.37% | 5.41% |

[a] Expressed as a weight percent olefinic unsaturation based on product at the stated time during the run.
[b] Diadduct was passed through a 10" × 1" diameter column of chi-alumina at 25° C., atmospheric pressure, and a rate of about 2 ml per ml of alumina per hour. The chi-alumina had a particle size of about 0.05 to 0.2 mm.
[c] Diadduct was passed through a 20" × 1" diameter column of chi-alumina at same conditions as in [b] with the same chi-alumina as in [b].
[d] Diadduct was passed through a 20" × 1" diameter column of gamma-alumina at the same conditions as in [b]. The gamma crystal form was identified by the X-ray pattern of the alumina and the particle size was about 0.04 to 0.17 mm.
[e] Diadduct was passed through a 20" × 1" diameter column of gamma-alumina at the same conditions as in [b]. The gamma-alumina was a commercially available chromatographic grade alumina with a particle size range of about 0.07 to 0.25 mm.
[f] Run terminated before this time.
[g] Samples not analyzed for the time period.

The results of these five runs shown in Table II illustrate that purification of diadduct with chi-alumina resulted in a product with a lower level of olefin unsaturation than was obtained when unpurified diadduct or diadduct passed through gamma-alumina was hydrogenated. In addition, purification of diadduct passed through larger quantities of chi-alumina resulted in even lower olefinic unsaturation of the product, as shown by the comparison of Run No. 5 using a 20 inch column of chi-alumina with Run No. 4 using a 10 inch column of chi-alumina.

Reasonable variations and modifications to the invention are possible within the scope of the foregoing disclosure and the appended claims.

That which is claimed is:

1. A process for the catalytic hydrogenation of an olefinically unsaturated dinitrile feedstock consisting essentially of the dinitrile reaction product obtained by contacting at least one olefinic hydrocarbon reactant, at least one olefinically unsaturated mononitrile reactant and at least one monoadduct reaction product of an olefinic hydrocarbon compound and an olefinically unsaturated mononitrile compound, each said olefinically unsaturated mononitrile reactant and each said olefinically unsaturated mononitrile compound containing a cyano group attached to a carbon atom adjacent and doubly bonded to a carbon atom which is attached to at least one hydrogen atom, each said olefinic hydrocarbon reactant and each said olefinic hydrocarbon compound having at least one olefinic linkage and having joined to one of the doubly bonded carbon atom another carbon atom having at least one hydrogen atom attached thereto, wherein said dinitrile reaction product comprises a mixture of 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile, which process comprises:

contacting said olefinically unsaturated dinitrile feedstock with chi-alumina so as to produce a treated feedstock; and subjecting said treated feedstock to suitable hydrogenation conditions in the presence of hydrogen and a suitable hydrogenation catalyst so as to effect hydrogenation of the olefinically unsaturated dinitrile compounds in said feedstock to the corresponding saturated dinitrile compounds and saturated diamine compounds.

2. A process in accordance with claim 1 wherein said catalyst comprises a catalyst component selected from the group consisting of elemental palladium and palladium compounds which are reducible by hydrogen to elemental palladium under said hydrogenation conditions, and mixtures of any two or more thereof together with a solid catalyst support thus forming a catalyst composition, the content of the elemental palladium in said catalyst composition being in the range of about 0.05 to about 20 weight percent of said catalyst composition.

3. A process in accordance with claim 1 wherein said catalyst comprises a catalyst component selected from the group consisting of elemental palladium and palladium compounds which are reducible by hydrogen to elemental palladium under said hydrogenation conditions, and mixtures of any two or more thereof.

4. A process in accordance with claim 3 wherein said olefinically unsaturated dinitrile feedstock is contacted under hydrogenation conditions with a diluent selected from the group consisting of alcohols having 1 to 12 carbon atoms per molecule, unsubstituted acyclic ethers having from 4 to 12 carbon atoms per molecule, unsubstituted cyclic ethers having from 4 to 12 carbon atoms per molecule, and mixtures of any two or more thereof.

5. A process in accordance with claim 4 wherein said diluent is methanol.

6. A process in accordance with claim 1 wherein said catalyst comprises a catalyst compound selected from the group consisting of elemental ruthenium and ruthenium compounds which are reducible by hydrogen to elemental ruthenium under said hydrogenation conditions, and mixtures of any two or more thereof, together with a solid catalyst support thus forming a catalyst composition, the content of the elemental ruthenium in said catalyst composition being in the range of about 0.05 to about 20 weight percent of said catalyst composition.

7. A process in accordance with claim 1 wherein said catalyst comprises a catalyst component selected from the group consisting of elemental ruthenium and ruthenium compounds which are reducible by hydrogen to elemental ruthenium under said hydrogenation conditions, and mixtures of any two or more therof.

8. A process in accordance with claim 7 wherein said olefinically unsaturated dinitrile feedstock is contacted under hydrogenation conditions with a diluent selected from the group consisting of alcohols having 2 to 12 carbon atoms per molecule, unsubstituted acyclic ethers having 4 to 12 carbon atoms per molecule, unsubstituted cyclic ethers having 4 to 12 carbon atoms per molecule, and mixtures of any two or more thereof.

9. A process in accordance with claim 8 wherein said diluent is tertiary-butyl alcohol.

10. A process in accordance with claim 7 wherein said olefinically unsaturated dinitrile feedstock is contacted under said hydrogenation conditions with ammonia so as to suppress undesirable formation of secondary and tertiary amines.

11. A process in accordance with claim 10 wherein the mol ratio of said ammonia to the cyano groups of said olefinically unsaturated dinitrile feedstock is in the range of about 1:1 to about 25:1.

12. A process in accordance with claim 3 or claim 7 wherein said solid support is selected from the group consisting of carbon, kieselguhr, silica, alumina, silica-alumina, calcium carbonate, asbestos, pumice, clays and mixtures of any two or more thereof.

13. A process in accordance with claim 3 or claim 7 wherein said solid support is gamma-alumina.

14. A process in accordance with claim 4 or claim 8 wherein said hyrogenation conditions comprise a hydrogen pressure in the range of about 500 to about 5000 psig (3.5 to 35 MPa); a temperature in the range of about 20° to about 250° C.; and a liquid hourly space velocity rate in the range of about 0.01 to about 10 volumes of unsaturated dinitrile plus diluent per volume of catalyst if conducted as a continuous process and, alternately, a reaction time in the range of about 15 minutes to about 5 hours if conducted as a batch process.

15. A process in accordance with claim 1 wherein said olefinically unsaturated dinitrile feedstock is brought into contact with said chi-alumina at a temperature in the range of about −10° to about 150° C.

16. A process in accordance with claim 1 or claim 15 wherein said olefinically unsaturated dinitrile feedstock is brought into contact with said chi-alumina in an inert atmosphere.

17. A process in accordance with claim 1 wherein said olefinically unsaturated dinitrile feedstock is brought into contact with said chi-alumina at a temperature in the range of from about −10° to about 150° C. and at a pressure in the range of from about 0.01 to about 100 atmospheres.

18. A process in accordance with claim 17 wherein said olefinically unsaturated dinitrile feedstock is fed through said chi-alumina at a flow rate in the range of from about 0.01 to about 50 ml of olefinically unsaturated dinitriles per ml of said chi-alumina per hour.

19. A process in accordance with claim 1 or claim 17 wherein said chi-alumina comprises particles of a size in the range from about 0.05 to about 0.2 mm.

* * * * *

UNITED STATES PATENT AND TRADEMARK OFFICE
CERTIFICATE OF CORRECTION

PATENT NO. : 4,235,808
DATED : November 25, 1980
INVENTOR(S) : Charles A. Drake

It is certified that error appears in the above–identified patent and that said Letters Patent are hereby corrected as shown below:

Column 6, claim 1, line 62, after "carbon" change "atom" to --- atoms ---.
Column 8, claim 8, line 1, after "under" insert --- said ---.

Signed and Sealed this

Seventeenth Day of March 1981

[SEAL]

Attest:

RENE D. TEGTMEYER

Attesting Officer

Acting Commissioner of Patents and Trademarks